United States Patent
Kubalak et al.

(10) Patent No.: US 6,887,230 B2
(45) Date of Patent: May 3, 2005

(54) URINE COLLECTION BAGS FOR URINARY CATHETER SYSTEMS

(75) Inventors: Thomas P. Kubalak, Plymouth, MN (US); Dennis Femrite, Andover, MN (US); Jerry R. Barber, Ventura, CA (US); Laura M. Calderon, Vandenberg AFB, CA (US); Ronald Crouther, Camarillo, CA (US); Christy R. Sweet, Santa Barbara, CA (US); Lawrence Y. Wissman, Santa Barbara, CA (US)

(73) Assignee: Mentor Corporation, Santa Barbara, CA (US)

(*) Notice: Subject to any disclaimer, the term of this patent is extended or adjusted under 35 U.S.C. 154(b) by 116 days.

(21) Appl. No.: 10/015,485

(22) Filed: Dec. 11, 2001

(65) Prior Publication Data

US 2002/0103460 A1 Aug. 1, 2002

Related U.S. Application Data

(63) Continuation-in-part of application No. 09/774,496, filed on Jan. 31, 2001.

(51) Int. Cl.[7] .................. A61M 27/00; A61M 25/00
(52) U.S. Cl. .................. 604/544; 604/192; 604/264
(58) Field of Search .................. 604/544, 327–331, 604/346–354, 317–326, 364, 192

(56) References Cited

U.S. PATENT DOCUMENTS

| | | |
|---|---|---|
| 2,329,360 A | 9/1943 | Salfisberg |
| 2,552,870 A | 5/1951 | Scherer |
| 2,856,932 A | 10/1958 | Griffitts |
| 3,035,691 A | 5/1962 | Rasmussen et al. |
| 3,345,988 A | 10/1967 | Vitello |
| 3,444,860 A | 5/1969 | Harrell |
| 3,474,786 A | 10/1969 | Spademan |
| 3,478,743 A | 11/1969 | Ericson |
| 3,529,599 A | 9/1970 | Folkman et al. |
| 3,537,109 A | 11/1970 | Spurrier et al. |

(Continued)

FOREIGN PATENT DOCUMENTS

| | | |
|---|---|---|
| AT | 3699994 | 2/1983 |
| EP | 0677299 | 10/1995 |
| FR | 2731345 | 9/1996 |
| GB | 2186233 A | 8/1987 |
| US | 1 493 257 | 11/1997 |
| WO | WO94/06377 | 3/1994 |
| WO | WO97/41811 | 11/1997 |
| WO | WO98/06642 | 2/1998 |
| WO | WO 00/16843 | 3/2000 |

OTHER PUBLICATIONS

Leroyer et al., "Prevention and Treatment of Urinary Infection in Patients with an Indwelling Catheter: Continuous Vesical Irrigation with a Mixed Antibiotic Solution of Neomycin and Polymyxin B," Ann.Anesth.Franc, 1979: 20(4), ps. 325–329.

Wu et al. "Catheter Kit: New Device for an Old Problem," *Archives of Physical Medicine and Rehabilitation*, 1980: 61(10), ps. 455–459.

(Continued)

*Primary Examiner*—John J. Calvert
*Assistant Examiner*—C. Lynne Anderson
(74) *Attorney, Agent, or Firm*—Fish & Richardson P.C., P.A.

(57) ABSTRACT

Urine collection bags are provided that include features that facilitate easy insertion of a urinary catheter into a patient's bladder. In some implementations, the urine collection bag is formed of a soft, flexible material that is comfortable when it contacts the user's skin, easy to manipulate, and relatively noiseless during use.

9 Claims, 10 Drawing Sheets

U.S. PATENT DOCUMENTS

| | | | |
|---|---|---|---|
| 3,556,294 A | | 1/1971 | Walck, III et al. |
| 3,642,126 A | | 2/1972 | Kurtz et al. |
| 3,648,704 A | | 3/1972 | Jackson |
| 3,794,042 A | | 2/1974 | De Klotz et al. |
| 3,841,332 A | | 10/1974 | Treacle |
| 3,854,483 A | | 12/1974 | Powers |
| 3,934,721 A | | 1/1976 | Juster et al. |
| 3,941,133 A | | 3/1976 | Chen |
| 3,961,529 A | | 6/1976 | Hanifl |
| 3,967,728 A | | 7/1976 | Gordon et al. |
| 4,000,649 A | | 1/1977 | Hanifl |
| 4,023,559 A | | 5/1977 | Gaskell |
| 4,062,363 A | | 12/1977 | Bonner, Jr. |
| 4,086,925 A | | 5/1978 | Dodge |
| 4,140,127 A | | 2/1979 | Cianci et al. |
| 4,157,709 A | | 6/1979 | Schuster et al. |
| 4,168,699 A | | 9/1979 | Hauser |
| 4,204,527 A | * | 5/1980 | Wu et al. .................... 600/575 |
| 4,230,115 A | | 10/1980 | Walz, Jr. et al. |
| 4,246,909 A | | 1/1981 | Wu et al. |
| RE30,607 E | | 5/1981 | Manschot et al. |
| 4,312,352 A | | 1/1982 | Meisch et al. |
| 4,363,406 A | | 12/1982 | Salvadori .................... 206/604 |
| 4,417,892 A | | 11/1983 | Meisch |
| 4,421,509 A | | 12/1983 | Schneider et al. |
| 4,534,766 A | * | 8/1985 | Steer et al. ................ 604/323 |
| 4,581,763 A | | 4/1986 | Olsen |
| 4,606,736 A | | 8/1986 | Van De Weghe |
| 4,622,033 A | | 11/1986 | Taniguchi |
| 4,629,159 A | | 12/1986 | Wellenstam |
| 4,652,259 A | | 3/1987 | O'Neil |
| 4,692,154 A | | 9/1987 | Singery et al. ............ 604/172 |
| 4,723,944 A | | 2/1988 | Jensen |
| 4,723,950 A | | 2/1988 | Lee |
| 4,754,877 A | | 7/1988 | Johansson et al. |
| 4,811,847 A | | 3/1989 | Reif et al. |
| 4,834,710 A | | 5/1989 | Fleck |
| 4,911,399 A | | 3/1990 | Green |
| 4,955,879 A | | 9/1990 | Mervine |
| 5,147,341 A | | 9/1992 | Starke et al. |
| 5,226,530 A | | 7/1993 | Golden |
| 5,242,398 A | | 9/1993 | Knoll et al. |
| 5,267,987 A | * | 12/1993 | Fabricant .................... 604/327 |
| 5,454,798 A | | 10/1995 | Kubalak et al. |
| 5,501,341 A | | 3/1996 | Van Es |
| 5,501,669 A | | 3/1996 | Conway et al. |
| 5,582,599 A | | 12/1996 | Daneshvar |
| 6,004,305 A | * | 12/1999 | Hursman et al. ........... 604/328 |
| 6,053,905 A | * | 4/2000 | Daignault et al. .......... 604/544 |
| 6,090,075 A | | 7/2000 | House |
| 6,402,726 B1 | * | 6/2002 | Genese ...................... 604/328 |
| 6,419,664 B1 | * | 7/2002 | von Bulow et al. ........ 604/337 |
| 6,482,190 B1 | | 11/2002 | Genese et al. |
| 6,579,709 B2 | | 6/2003 | Guegler et al. |
| 2002/0103460 A1 | | 8/2002 | Kubalak et al. |
| 2003/0060807 A1 | | 3/2003 | Tanghoj et al. |

OTHER PUBLICATIONS

Nolph et al, "Continuous Ambulatory Peritoneal Dialysis," *The New England Journal of Medicine*, 1988: 318(14), ps. 1595—1600.

http://www.ncbi.nlm.nih.gov/entrez/query.fcgi?cmd+Retrieve&db+PubMed&list_uids+1752267&dopt+Abstract—Hellstrom et al., "Efficacy and Safety of Clean Intermittent catheterization in Adults (abstract)," article dated 1991, printed from the Internet on Jul. 17, 2003, 1 p.

http://www.ncbi.nlm.nib.gov/entrez/query.fcgi?cmd+Retrieve&db+PubMed&list_uids+7815580&dopt+Abstract—Diokno et al., "Patient Satisfaction and the LoFric Catheter for Clean Intermittent Catheterization (abstract)," article dated 1995, printed from the Internet on Jul. 17, 2003, 1 p.

Miyazaki et al., "Intermittent Self–Catheterization Set," *Japanese Journal of Clinical Urology*, 1998: 34(7), ps. 663—665.

Nichols et al., "Paediatric Spina Bifida Patients and Pre–Lubricated Intermittent Catheter Use," 2002, 1 p.

http://www.multi-sclerosis.org/news/Jan2002/CathetersPreventingBladderInfections.html—Vogel, "Preventing Antibiotic–Resistant Bladder Infections," 2002, 3 ps.

http://www.internurse.com/products/products/entries/instantcath.html—Easton, "InstantCath from Hollister: pre–lubricated self–catheterization," undated, 7 ps.

PCT Search Report.

* cited by examiner

URINE COLLECTION BAGS FOR URINARY CATHETER SYSTEMS

CROSS-REFERENCE TO RELATED APPLICATIONS

This application is a continuation-in-part application of and claims priority to U.S. application Ser. No. 09/774,496, filed on Jan. 31, 2001.

TECHNICAL FIELD

This invention relates to urine collection bags for urinary catheter systems.

BACKGROUND

Urinary catheter systems generally include a long, thin, flexible tube (the urinary catheter) that is inserted into the urethra, past the trigone muscle and into the bladder to withdraw urine from the bladder. Urine flows through the catheter and is collected, e.g., in a urine collection bag. Once urine flow stops, or if the bag is filled, the catheter is removed from the bladder. The catheter is generally lubricated to facilitate insertion. In a closed catheter system, the lubricated catheter is supplied inside the urine collection bag with a urethral introducer tip to prevent human contact/ contamination of the catheter as it is inserted into the urethra. The introducer tip is inserted into the patient's urethra, and the catheter is advanced out of the bag by sliding the catheter through the bag using the following procedure. Following insertion of the introducer tip, the user stabilizes the introducer tip with the user's non-dominant hand (i.e., the left hand if the user is right-handed). Next, using his dominant hand, the user holds the catheter through the bag, with his thumb and index finger, just behind the introducer tip, and advances the catheter slowly into the urethra. The catheter is advanced by the user pinching the catheter with his non-dominant hand, while using his dominant hand to retract the bag without retracting the catheter out of the urethra. The user then reduces the finger pressure applied by the non-dominant hand, and repeats the preceding step a number of times until the catheter has been advanced into the bladder and urine is flowing into the bag.

There is a tendency, during this procedure, for the catheter to slip back into the bag as the user is trying to advance it, causing the user discomfort and frustration. This is in part due to the difficulty of gripping the lubricated catheter through the bag material. Many users of urinary catheters have compromised finger strength, due to spinal cord injuries, which only exacerbates the gripping problem. Also, if the bag is formed of certain materials, moving the bag in this manner may cause a "crinkling" noise that may be embarrassing to the user if the catheter is being used in a public restroom.

SUMMARY

The present invention provides a urine collection bag that includes features that facilitate easy insertion of a urinary catheter into a patient's bladder. In some implementations, the urine collection bag is formed of a soft, flexible material that is comfortable when it contacts the user's skin, easy to manipulate, and relatively noiseless during use. Thus, the urine collection bag can be used with a minimum of discomfort, and can be used discreetly in public restrooms. In some implementations, the urine collection bag is formed of a material that includes a surface texture that will allow the user to more easily grip the catheter through the bag material. In some implementations, the bag has an elongated neck and smoothly rounded shoulders, to improve user comfort by reducing chafing of the bag against the user's legs, and eliminating sharp corners that could jab a user.

In one aspect, the invention features a urine collection bag for use in a urinary catheter system, including opposed portions of plastic sheet material that are sealed together around a peripheral edge to define a substantially closed receptacle, each portion including a surface texture having a depth sufficient to increase the flexibility of the plastic sheet material relative to an otherwise identical plastic sheet material without the surface texture.

Implementations of this aspect of the invention may include one or more of the following features. The surface texture is provided on the opposed surfaces of the portions. The depth of the surface texture is selected to provide the plastic sheet material with a hardness of less than about 85 Shore A. The minimum depth of the surface texture is at least about 25% of the thickness of the plastic sheet material. The depth of the surface texture is preferably from about 25% to 75% of the thickness of the plastic sheet material. More preferably, the depth of the surface texture is from about 40% to 60% of the thickness of the plastic sheet material. The plastic sheet material includes polyvinyl chloride. The plastic sheet material has an overall thickness of from about 5 to 10 mils. The surface texture provides the sheet material with a hardness of from about 60 to 85 Shore A.

In another aspect, the invention features a urine collection bag for use in a urinary catheter system, including opposed portions of plastic sheet material that are sealed together around a peripheral edge to define a substantially closed bag, a surface texture being disposed on the opposed surfaces of each of the portions.

In some implementations of this aspect of the invention the plastic sheet material includes polyethylene. Preferably, the surface texture is constructed to increase the friction between the opposed surfaces of the portions and a catheter during gripping of the catheter by a patient, relative to the friction exerted by opposed portions of an otherwise identical plastic sheet material without the surface texture.

In a further aspect, the invention features a urine collection bag for use in a urinary catheter system including a catheter having an introducer tip for introduction of the catheter into the urethra. The urine collection bag includes opposed portions of plastic sheet material that are sealed together around a peripheral edge to define a substantially closed receptacle, the receptacle having an open end through which the catheter can be advanced into the urethra, and, joined to the receptacle at the open end, a braking interface tube constructed to receive and guide the introducer tip, the braking interface tube having a beveled leading edge.

Implementations of this aspect of the invention may include one or more of the following features. The leading edge is inclined at an angle of from about 15 to 45 degrees. Facing surfaces of the opposed portions of plastic sheet material include a surface texture. The braking interface tube is formed from a polymer selected from the group consisting of polyvinyl chloride, polyurethanes and silicones. The braking interface tube is formed of a material having a hardness of from about 40 to 80 Shore A. The beveled leading edge defines an open area, and the braking interface tube is dimensioned and positioned so as to allow a user to place his thumb against a first one of the opposed portions, over the open area, and his index finger on the opposite one of the opposed portions, approximately aligned with the thumb, so that the thumb presses the first opposed portion directly against the catheter tube, while the index finger presses the opposite opposed portion against a lower surface of the braking interface tube, which in turn presses against the catheter tube. The open area is substantially elliptical.

In yet another aspect, the invention features a urine collection bag for use in a urinary catheter system including a catheter having an introducer tip for introduction of the catheter into the urethra, the urine collection bag including (a) opposed portions of plastic sheet material that are sealed together around a peripheral edge to define a substantially closed receptacle, the receptacle having an open end through which the catheter can be advanced into the urethra; and (b) joined to the receptacle at the open end, a braking interface tube constructed to receive and guide the introducer tip, the braking interface tube being formed of a material having a hardness of from about 40 to 70 Shore A.

In some implementations of this aspect of the invention the braking interface tube is formed of polyvinyl chloride.

The invention also features a urine collection bag for use in a urinary catheter system, including opposed portions of plastic sheet material that are sealed together around a peripheral edge to define a substantially closed receptacle, the plastic sheet material being a noiseless material, i.e., a material that makes substantially no audible crinkling noise when the urine collection bag is manipulated during ordinary use.

In another aspect, the invention features a urine collection bag for use in a urinary catheter system, including opposed portions of a polyvinyl chloride plastic sheet material having a thickness of from about 5 to 10 mils, the opposed portions being sealed together around a peripheral edge to define a substantially closed receptacle.

In a further aspect, the invention features a urine collection bag for use in a urinary catheter system, including opposed portions of plastic sheet material that are sealed together around a peripheral edge to define a substantially closed, substantially bottle-shaped receptacle.

Implementations of this aspect of the invention may include one or more of the following features. The receptacle includes an elongated neck region, having a width of less than about 50 mm. The receptacle includes curved shoulders. The shoulders have a radius of curvature of from about 0.25 to 1.03 degrees. The receptacle has a total volume of at least 1000 cc.

The invention also features a urine collection bag for use in a urinary catheter system, including (a) opposed portions of plastic sheet material that are sealed together around a peripheral edge to define a substantially closed receptacle, each portion including a surface texture having a depth sufficient to increase the flexibility of the plastic sheet material relative to an otherwise identical plastic sheet material without the surface texture, the surface texture being disposed on an interior surface of the receptacle; and (b) an interface tube having a beveled opening constructed to allow a user to apply pressure with an index finger or thumb from an exterior surface of the receptacle and thereby press the surface texture against a urinary catheter disposed within the receptacle to hold the catheter in place while manipulating the sheet material to advance the catheter out of the receptacle.

In some implementations of this aspect of the invention, the sheet material is a noiseless material, e.g., polyvinyl chloride.

The invention also features closed catheter systems including the urine collection bags described above.

Figure 4:
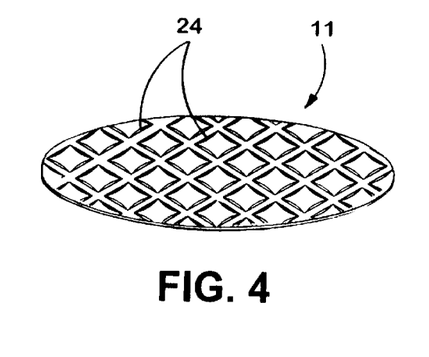
FIG. 4 is a highly enlarged, detail top view of the surface texture of a film that is suitable for use in the urine collection bag shown in FIG. 1.
Figure 4A:
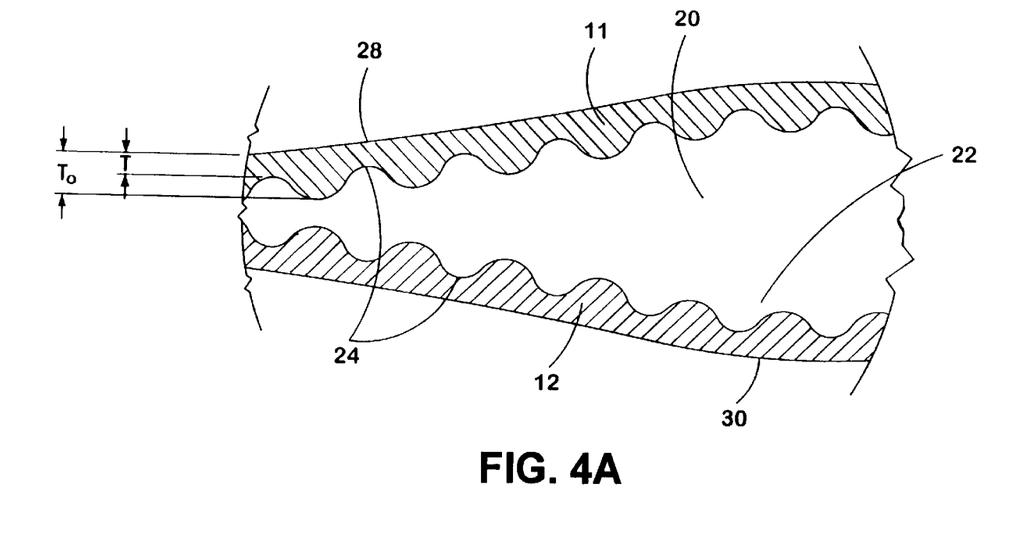
FIG. 4A is a highly enlarged detail cross-sectional view of a portion of the bag, illustrating the opposed textured surfaces.

The term "overall thickness", when used herein to refer to a textured film, refers to the thickness of the film including the raised areas of the surface texture (e.g., dimension $T_O$ in FIG. 4A). If the textured film includes a surface texture having raised areas of different heights, the overall thickness is measured at the highest point on the textured surface.

Other features and advantages of the invention will be apparent from the description and drawings, and from the claims.

DETAILED DESCRIPTION

Figure 1:
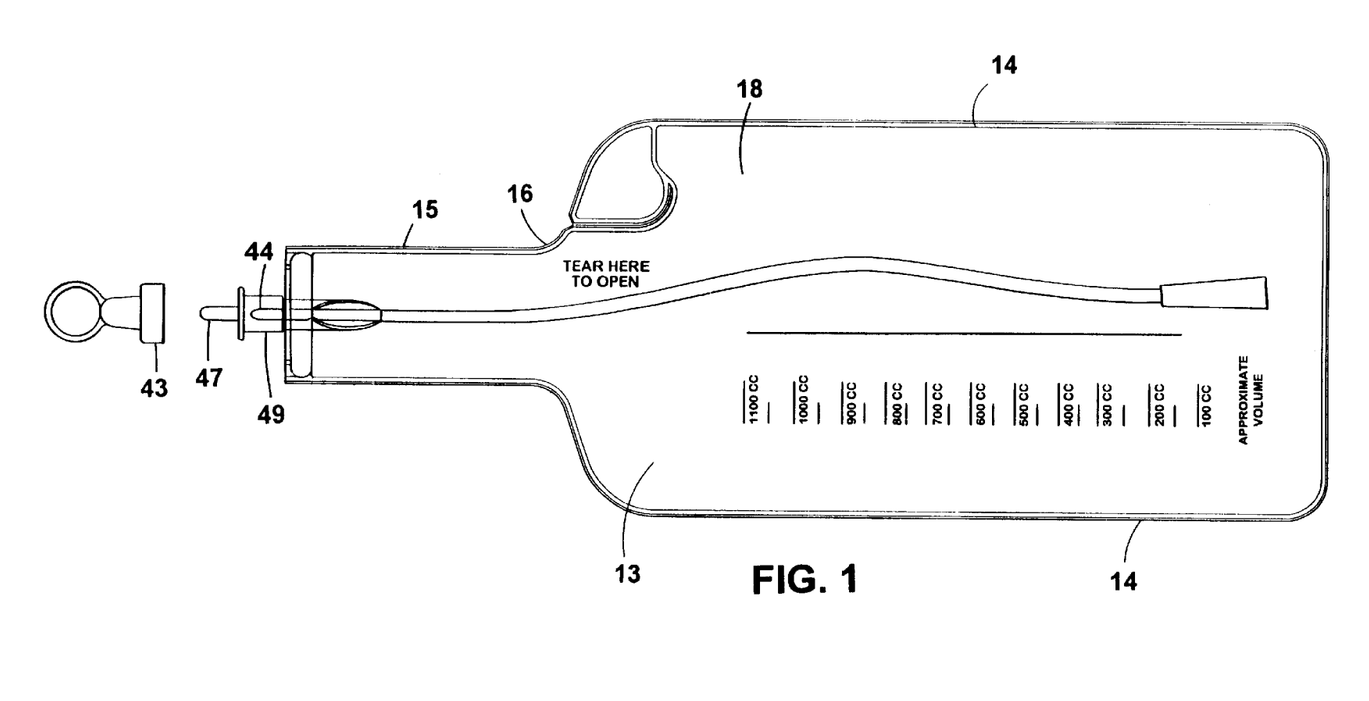
FIG. 1 is a front planar view of a urine collection bag according to one embodiment of the invention, with a catheter shown in phantom lines within the urine collection bag.
Figure 1A:
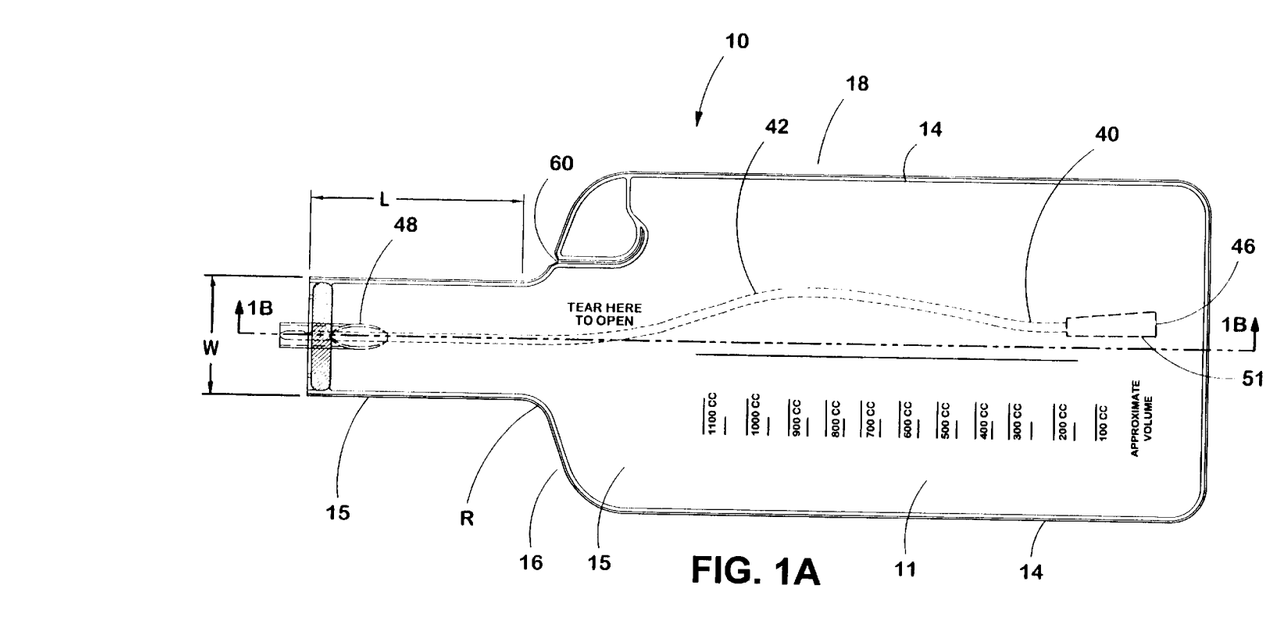
FIG. 1A is similar to FIG. 1, except that the cap and catheter guide have been omitted to more clearly show the braking interface tube.
Figure 1B:
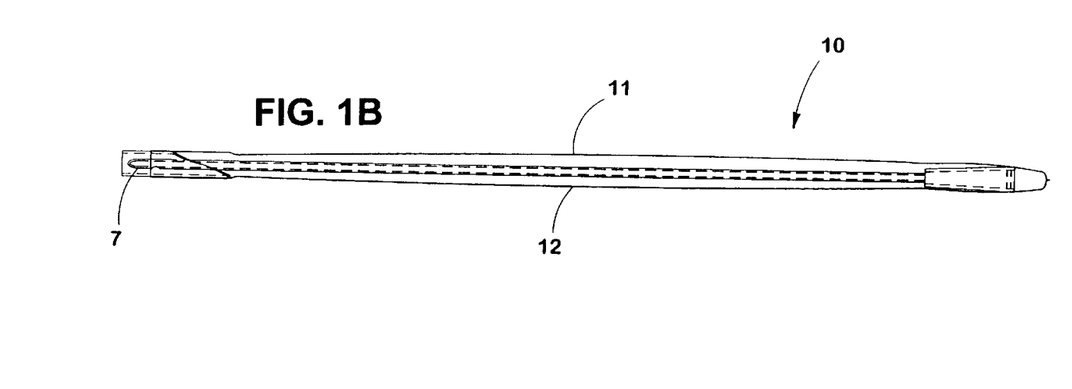
FIG. 1B is a cross-sectional view of the bag, taken along line B—B in FIG. 1A (for clarity, the catheter is shown as if it were extended straight along line B—B in FIG. 1A).

Referring to FIGS. 1, 1A and 1B, a urine collection bag 10 includes two opposed portions 11 and 12 of flexible sheet material (FIG. 1B), which are sealed at seams 14 to provide a substantially closed receptacle 13 for receiving urine flowing from the bladder of a patient. Seams 14 can be sealed, e.g., by ultrasonic welding or heat sealing. Prior to use, a catheter 40 (shown in phantom lines) resides in the urine collection bag 10. The catheter 40 includes a catheter tube 42 with a first end 44 for insertion into the patient's urethra and a second end 46 through which urine from the bladder flows into the bag 10. The first end 44 of the catheter tube 42 includes an introducer tip 47 that resides in a braking interface tube 48 that is welded to the base of the introducer tip 47. The function of braking interface tube 48 will be described in detail below. The second end 46 of the catheter tube 42 includes a rigid, non-deformable stop member 51 designed to prevent the catheter 40 from slipping out of the bag 10 through the interface tube opening 50 when the catheter is in use. A cap 43 is provided to seal the bag before and after use. The receptacle 13 may be substantially "bottle-shaped", i.e., it has an elongated, relatively narrow neck region 15, shoulders 16, and a relatively wide reservoir region 18. The neck region 15 preferably has a width W (FIG. 1A) of less than about 5 cm, more preferably from about 4 to 6 cm, and a length L of at least about 8 cm, more preferably about 8 to 12 cm.

Shoulders 16 are smoothly curved, and preferably have a radius of curvature R of from about 0.25" to 1.03". This shape has been found to generally improve user comfort by minimizing chafing and discomfort that can result from sharp edges and corners. While the receptacle may have any desired volume, the receptacle generally has a volume of at least 1000 cc.

Preferably, as shown in FIGS. 4 and 4A, the inner surfaces 20, 22 of the portions 11, 12, include a surface texture, e.g., a diamond shaped pattern as shown in FIG. 4. The surface 10 texture provides the inner surfaces with a plurality of depressed areas 24 which have a thickness T that is reduced relative to the overall thickness $T_o$ of the sheet material. The surface texture of the sheet material serves two purposes. First, the depressed areas 24 function as hinge points, significantly increasing the flexibility of the sheet material. This increase in flexibility is advantageous if the sheet material to be used is inflexible, and/or if it is desired to use a relatively thick sheet material, e.g., for ease of processing or strength considerations. Second, the surface texture improves the ability of the user to grip the catheter through the bag when advancing the catheter as described above in the Background section. As discussed above, it is often difficult for a user to grasp a slippery, lubricated catheter through the sheet material. Providing a surface texture increases the surface area that is available, improving gripping. Moreover, during gripping the depressed areas 24 act as storage pockets to receive the lubricant, and the raised areas in between act as pressure points that grip the catheter.

The surface texture is preferably on the inner surfaces 20 and 22 in order to provide this improved gripping; however, the surface texture can be provided on both the inner surfaces and the outer surfaces 28 and 30, or only on the outer surface if the improved gripping feature is not required.

The depth of the surface texture, i.e., the difference between $T_o$ and T, will depend upon the degree of increased flexibility that is desired, which will in turn generally depend on the stiffness of the sheet material prior to imparting the surface texture. The two primary variables that will affect the stiffness of the sheet material are the thickness of the sheet material ($T_o$) and its hardness. The thicker and the harder the material, the stiffer it will be in use. Generally, it is preferred that the surface texture have a depth of at least 25% of the thickness $T_o$, and preferably from 40 to 60%. If the plastic sheet material has an initial hardness (prior to imparting the surface texture) of from about 60 to 80 Shore A, and a thickness of from about 5 to 10 mils, the depth will generally be from about 40 to 60%. If increased flexibility is not required, e.g., if a flexible material such as polyethylene is used, the depth of the surface texture need only be sufficient to provide improved gripping.

Preferred plastic sheet materials include extrudable thermoplastics such as polyvinyl chloride (PVC), high and low density polyethylenes, and polypropylenes. PVC is preferred in some implementations, due to its flexibility, softness, ease of processing, and biocompatibility and hypoallergenic qualities. A suitable PVC is 78 Shore A Polyvinyl Chloride PVC 2222 FS/1-78 Clear 0202, commercially available from Alpha Gary corporation. Suitable plastic sheet materials are manufactured with grades of polymer suitable for human contact. Preferably, after the surface texture is imparted the sheet material has a hardness of from about 60 to 85 Shore A, more preferably about 75 to 81 Shore A. The hardness of the material will determine, in addition to its flexibility, the amount of "crinkling" sound that is produced when the bag is manipulated. If the sheet material is too hard, the bag will tend to make an undesirable amount of noise when used, and may be difficult to manipulate. If it is too soft, the material may have a tendency to elongate under a load, thus distorting the accuracy of the bag markings for fluid intake measurement. Some polyethylenes tend to be "noisy" when used in bags. If polyethylene is used, it is preferred that a relatively quiet grade be selected.

Generally, preferred sheet materials have a thickness of from about 5 to 10 mils. If the sheet material is too thin, it may be difficult to form seal 14 (seal the edges of the portions to form the receptacle), while if it is too thick it may be difficult to obtain a desired flexibility.

A suitable surface texture is shown schematically in FIGS. 4–4A. This surface texture is formed of a crisscrossed arrangement of linear depressed areas, creating a pattern of generally diamond-shaped raised areas. Many other surface textures may be used, provided the desired degree of flexibility and/or gripping is provided. Other suitable surface textures can be readily determined by those skilled in the art, and include any texture that can be applied to the surface of a metal roll, including but not limited to squares, rectangles, triangles, ellipses, polygons, circles, crystals, snowflakes.

The surface texture may be imparted by extruding the sheet material and then passing it between a set of textured rollers prior to winding it up on a take-up roll, or using any other desired technique.

The Braking Interface Tube

Figure 2:
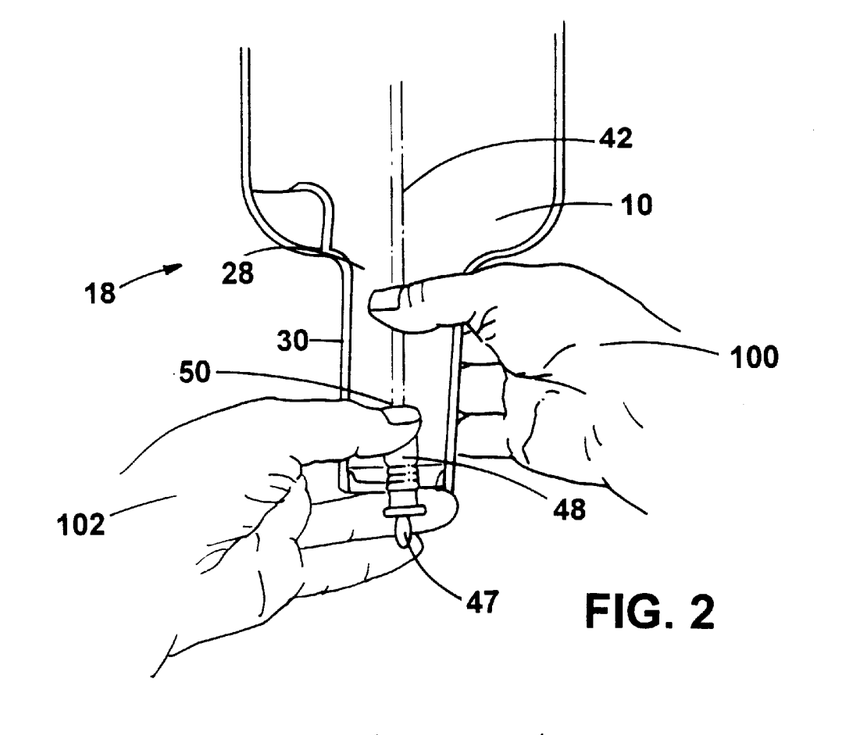
FIGS. 2–2A are schematic perspective views showing a user of the urine collection bag shown in FIG. 1 advancing the catheter out of the bag.
Figure 2A:
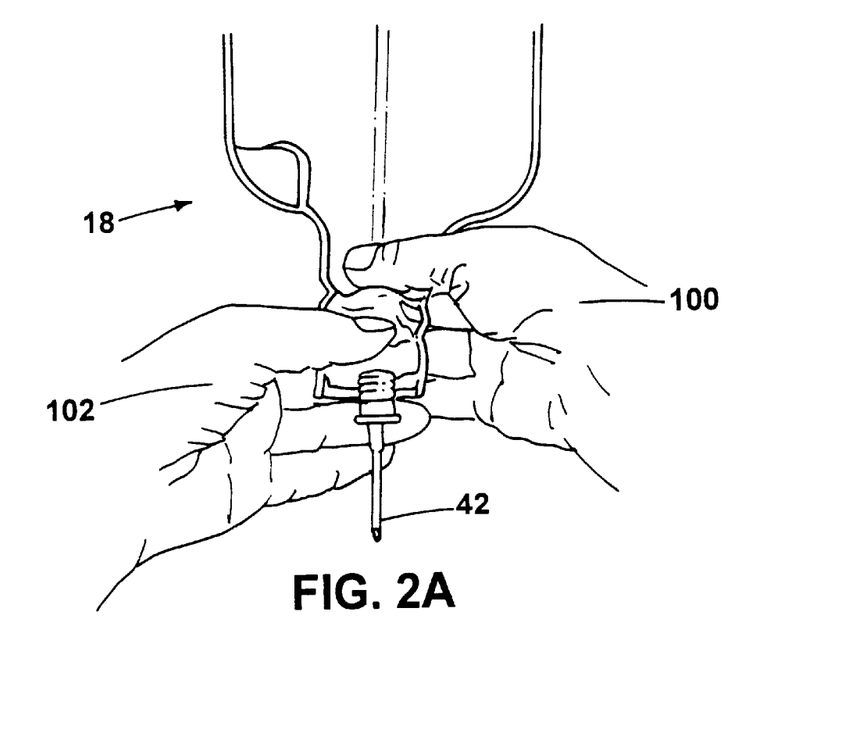

To use the urinary catheter 40, the introducer tip 47 is inserted into the patient's urethra, and the catheter is advanced out of the urine collection bag 10 by sliding the catheter through the bag using the following procedure. Following insertion of the introducer tip 47, the user stabilizes the introducer tip with the user's non-dominant hand 102, as shown in FIG. 2. Next, using his dominant hand 100, the user holds the catheter tube 42 through the bag, with his thumb and index finger, about 1 to 2 inches behind the braking interface tube 48 (discussed below), and advances the catheter tube 42 slowly into the urethra. As shown in FIG. 2A, the catheter tube 42 is advanced by the user squeezing the catheter tube 42 with his non-dominant hand 102, while using his dominant hand 100 to retract the bag 10 without retracting the catheter tip 44 out of the urethra. The user then reduces the finger pressure applied by the non-dominant hand, and repeats the preceding step a number of times until the catheter has been advanced into the bladder and urine is flowing into the bag. During this procedure, the non-dominant hand grasps the catheter tube 42 using the braking interface tube 48. The braking interface tube 48 includes an opening 50 having a beveled leading edge that is inclined at an angle A (FIG. 3A) of from about 15 to 45 degrees from the horizontal H (a horizontal line taken along the upper surface 52 of braking interface tube 48 at the apex X of the beveled leading edge. If the beveled edge is formed by cutting the tube, angle A will typically vary to some extent from the angle at which the tube is cut, due to flattening and distortion of the soft tube during cutting.

Figure 3:
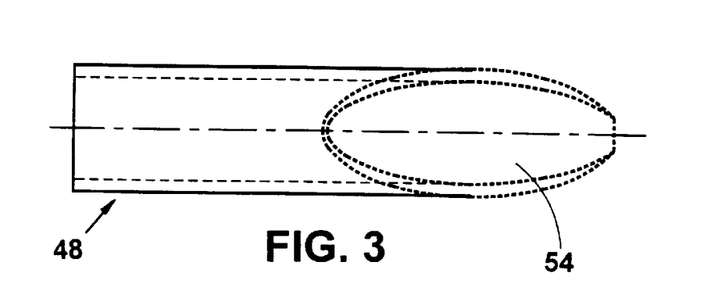
FIGS. 3, 3A and 3B are, respectively, enlarged top, side and end views of a braking interface tube used in the urine collection bag shown in FIG. 1.
Figure 3A:
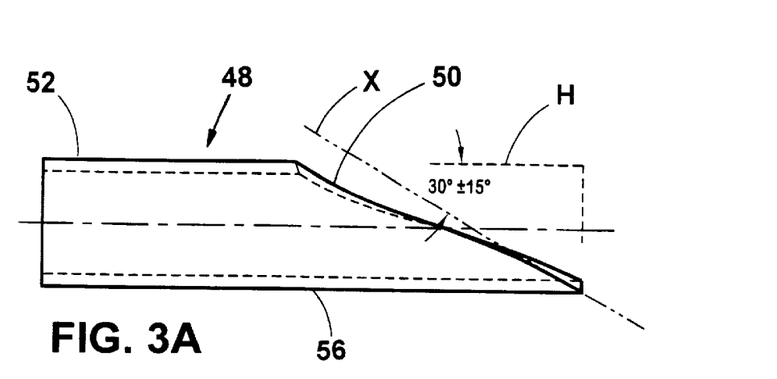
Figure 3B:
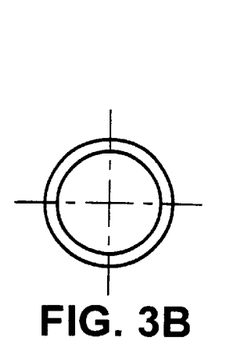

This beveled leading edge provides a generally elliptical open area 54. When the user grasps the catheter tube 42 with the non-dominant hand, the user places his thumb against the bag portion 11, over either the open area 54 or the upper surface 52, and his index finger on the opposite side of the bag, against bag portion 12, approximately aligned with the thumb. Thus, the thumb presses the bag portion 11 directly against the catheter tube 42, while the index finger presses the bag 12 against a lower surface 56 of the braking interface tube, which in turn presses against the catheter tube 42. When the user desires to stop the movement of the catheter tube, the user presses the thumb and index finger together to squeeze the braking interface tube against the catheter tube. The inventor has found that the beveled geometry of the braking interface tube, and the manner in which it is positioned, allows the user to securely grasp the catheter tube 42 through the bag during step (b), providing a "braking" effect which generally prevents the tube from slipping back into the bag during this step. The ability to effectively brake the catheter tube during advancement improves user comfort and ease of insertion. Also, the beveled edge of opening 50 acts as a contoured stop to allow complete advancement of the catheter using the textured film, without an abrupt stopping point. This feature maximizes stroke length (the distance the catheter can be moved during a single advancement step) and control of the catheter during the insertion process.

The beveled edge of the tube also acts as a leak resistant seat for the small diameter of the deformable stop member 51 when the catheter is completely extended out of the bag. Due to this sealing feature, leakage of fluid out of the introducer tip onto the patient and the patient's clothes or bedding is minimized or eliminated altogether. Due to the presence of lubricant, the deformable stop member 51 can be easily disengaged from the beveled edge when the user desires to do so.

A braking interface tube 48 can be provided in a urine collection bag that does not include the textured surfaces described above. However, it is preferred that the bag include both of these features, since the textured surface enhances the braking effect that is provided by squeezing the braking interface tube and the flexible sheet material.

Suitable materials for the braking interface tube include resilient thermoplastics such as PVC, polyethylene, polyurethanes, silicones and coextrusions of these materials. A preferred material is PVC, a suitable grade of which is a medical grade USP Class VI, commercially available from Alpha Gary Corporation, as product no. 2222C-65. Preferred materials have a hardness of less than about 80 Shore A, more preferably from about 40 to 80 Shore A, and most preferably from about 50 to 70 Shore A. Generally, the tube will have a wall thickness of from about 0.89 to 1.02 mm. Typically, the thicker the wall thickness, the softer the tube material should be. The hardness and wall thickness are selected so that the user can easily pinch the walls of the braking interface tube together with finger pressure to grip the catheter tube as stated above.

Using the Closed Catheter System

To obtain a urine sample, the catheter 40 is advanced through the braking interface tube 48 and out of the introducer tip 47, as discussed above, and is inserted into the urethra of the patient. The catheter 40 is then gradually moved into the urethra until the catheter reaches the bladder and urine begins to flow into the bag 10. Following use, the bag 10 may be torn at a tear seam 60 at the base of the bag neck on the shoulder. The urine in the bag 10 may then be poured from the bag into a sample collection vessel for analysis.

Other embodiments are within the scope of the following claims.

Figure 5:
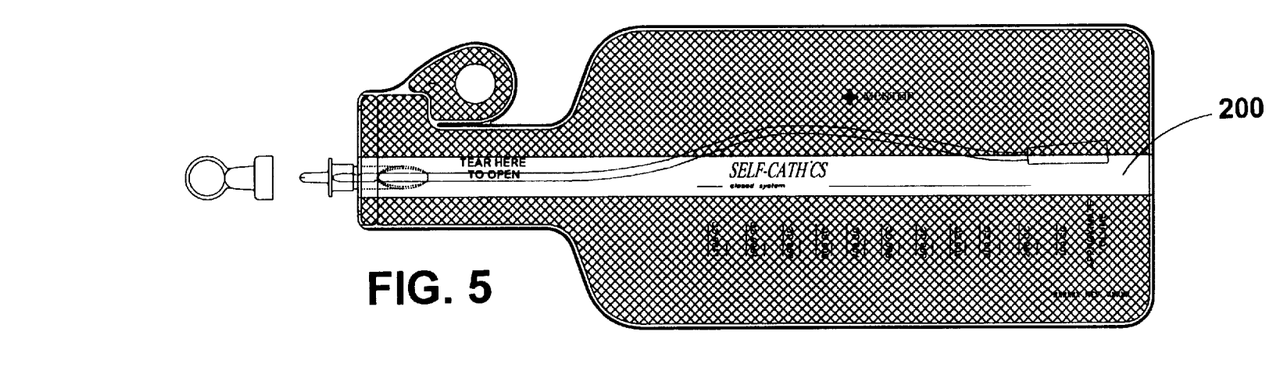
FIGS. 5 and 5A are front planar views of urine collection bags according to alternate embodiments of the invention.
Figure 5A:
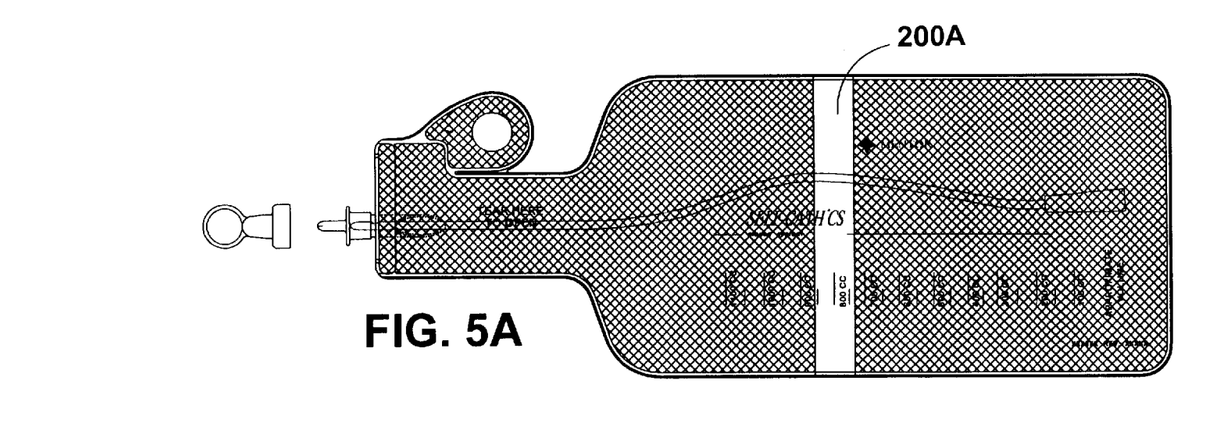

For example, if the surface texture tends to render the bag translucent or opaque, it may be desirable to provide a clear window in one or both of portions 11 and 12. (The degree of visibility through the textured film will generally depend on the depth of the texture, the clarity of the plastic and the manufacturing process used.) This may be accomplished by, for example, selectively texturing the film in the machine direction during the film extrusion process. To simplify processing, the window may be in the form of a continuous clear stripe, e.g., longitudinal stripe 200 in FIG. 5 or width-wise stripe 200A in FIG. 5A.

This window allows the user to improve his view of his urine and evaluate whether it is too dark, cloudy, or has particulate matter floating in it, indicating that the user should drink more water as a first line of defense against a urinary tract infection (UTI). Having a visual warning can often allow the user to ward off a UTI by taking early countermeasures.

An alternative to a clear window or stripe is to texturize only one of the portions 10, 12, and leave the other portion untextured.

Figure 6:
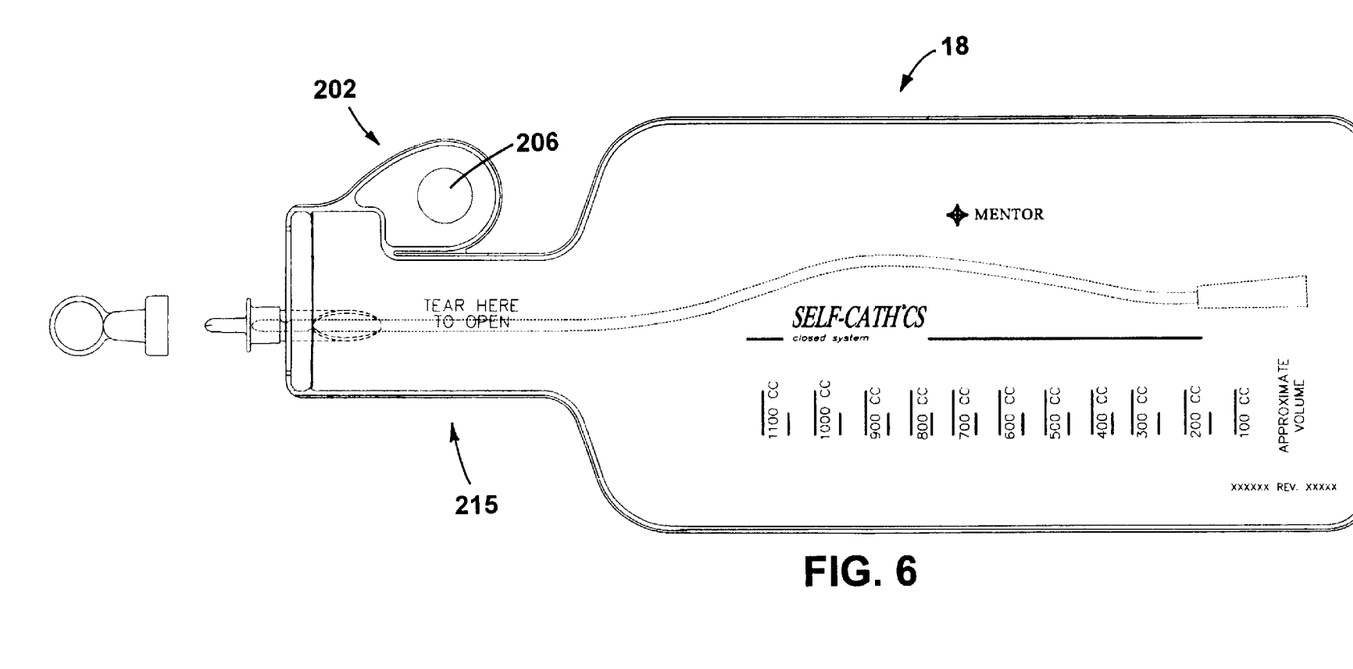
FIG. 6 is a front planar view of a urine collection bag according to an alternate embodiment of the invention.

Moreover, the tear seam 60, shown on the side of the reservoir region 18 in FIG. 1, may be positioned in other areas of the bag, to facilitate draining of urine from the bag. For example, as shown in FIG. 6, a tear tab 202 may be positioned on the neck region 215 of the bag. This positioning allows a pour opening 204 (FIG. 7A) to be provided on the side of the neck region, rather than on the side of reservoir region 18, as would be the case in the embodiment shown in FIG. 1.

Figure 7:
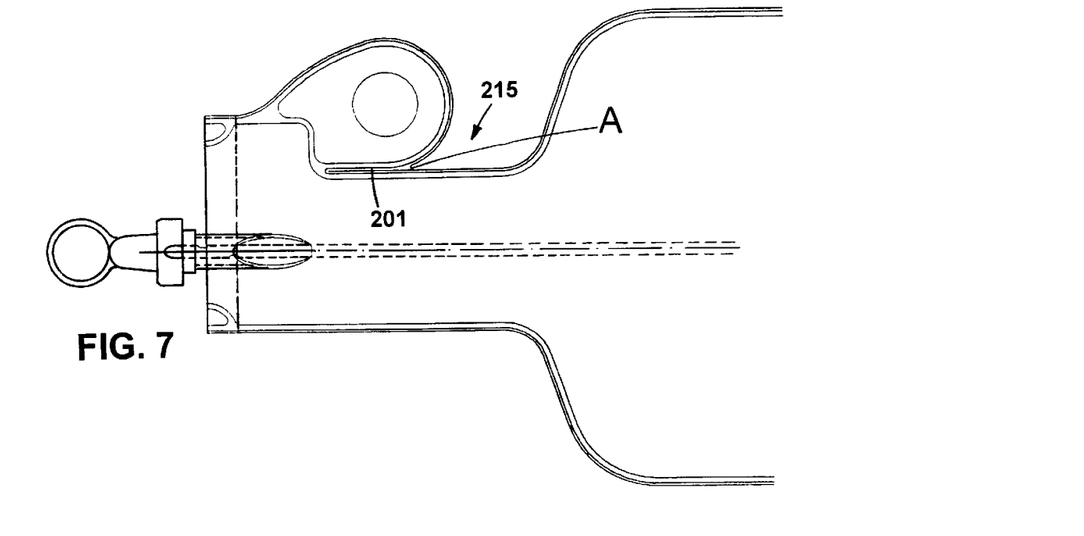
FIG. 7 is a partial front planar view of a urine collection bag according to an alternate embodiment of the invention, similar to that shown in FIG. 6.
Figure 7A:
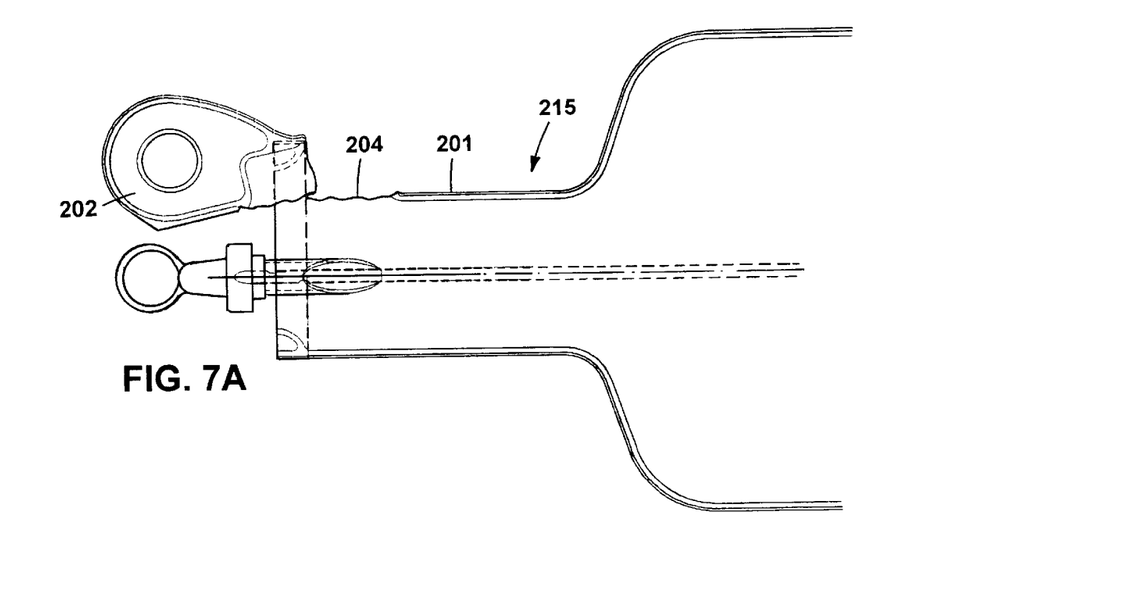
FIG. 7A shows the urine collection bag of FIG. 7 with the tear tab separated from the bag.

Preferably, the tear tab 202 is detachably joined to the neck 215 by a recessed groove 201 which allows the tear tab to be smoothly torn towards the user (out of the page, in FIG. 7) to the position shown in FIG. 7A, resulting in pour opening 204. Tearing is initiated at a notch A (FIG. 7). Pour opening 204 generally has a nominal length of from about 0.75 to 1.25 inch, resulting in an opening having a diameter of about 0.45 to 0.8 inch, assuming the opening to be circular (in practice, it is typically somewhat elliptical).

Providing the pour opening on the neck of the bag generally allows the user or a caregiver to drain the bag by holding the reservoir region and tilting the pour opening downward. Using one hand to drain the bag allows a wheelchair-bound patient to use the other hand to hold onto his wheelchair. The positioning of the tear tab on the side of the neck, with the tear direction being away from the patient, allows the patient to use the weight of the urine-filled bag to his advantage, rather than against him as would be the case with other tear tab locations.

An alternate arrangement that allows the bag to be drained using one hand is to position the tear tab at the bottom of reservoir region 18. In this case, the user would generally grasp the neck region to drain the bag.

Figure 8:
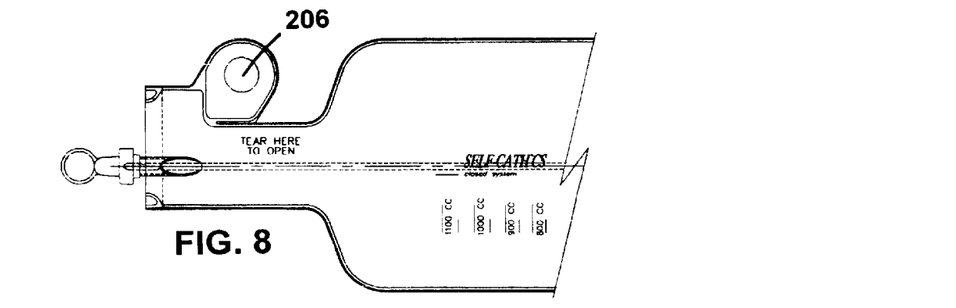
FIGS. 8–8C are partial front planar views of urine collection bags according to other alternate embodiments of the invention, having alternate tear tab designs.
Figure 8A:
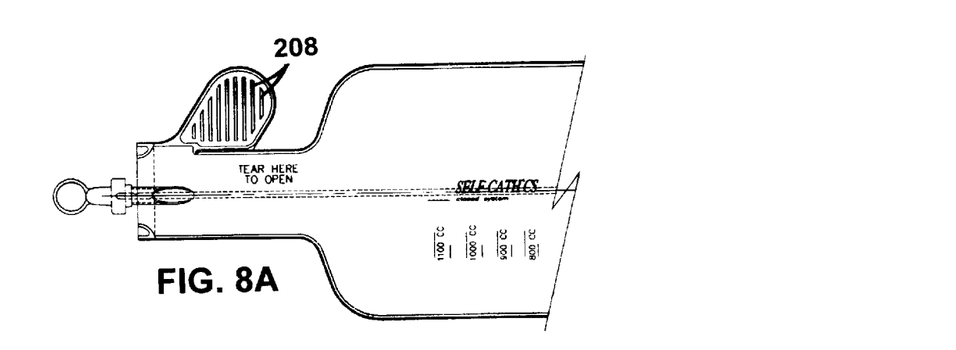
Figure 8B:
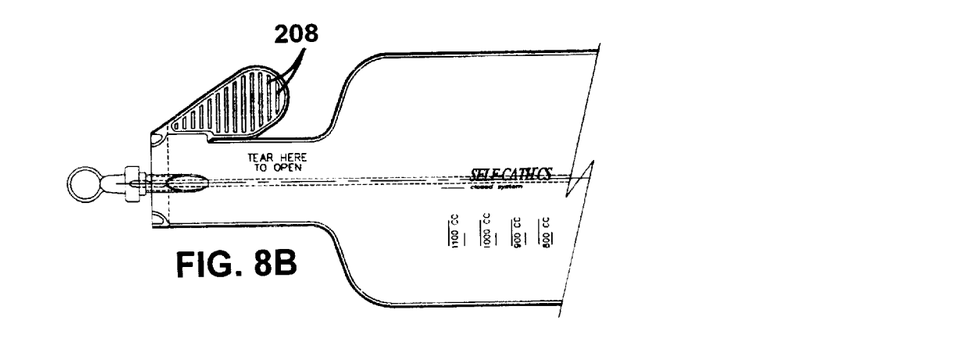
Figure 8C:
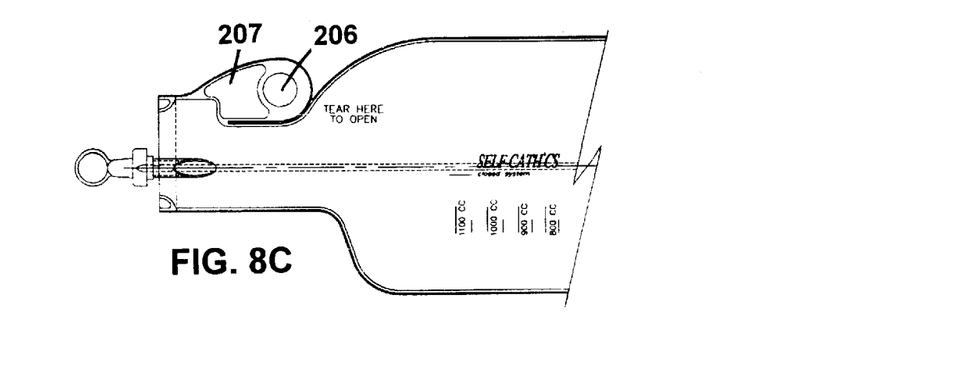

The tear tab may have any desired design. Examples of suitable designs that allow easy removal of the tear tab (as shown in FIG. 7A), while preventing inadvertent removal and bag leakage, are shown in FIGS. 6, 7 and 8–8C. The tear tab may have a hole through which the user may insert his finger to pull the tab, e.g., holes 206 in FIGS. 6, 7, 8 and 8C. The tear tab shown in FIG. 8C includes a recessed area 207, to facilitate gripping. Alternatively, the tear tab may include raised ribs or other structures to assist the user in gripping the tab, e.g., ribs 208 in FIGS. 8A and 8B.

Figure 9:
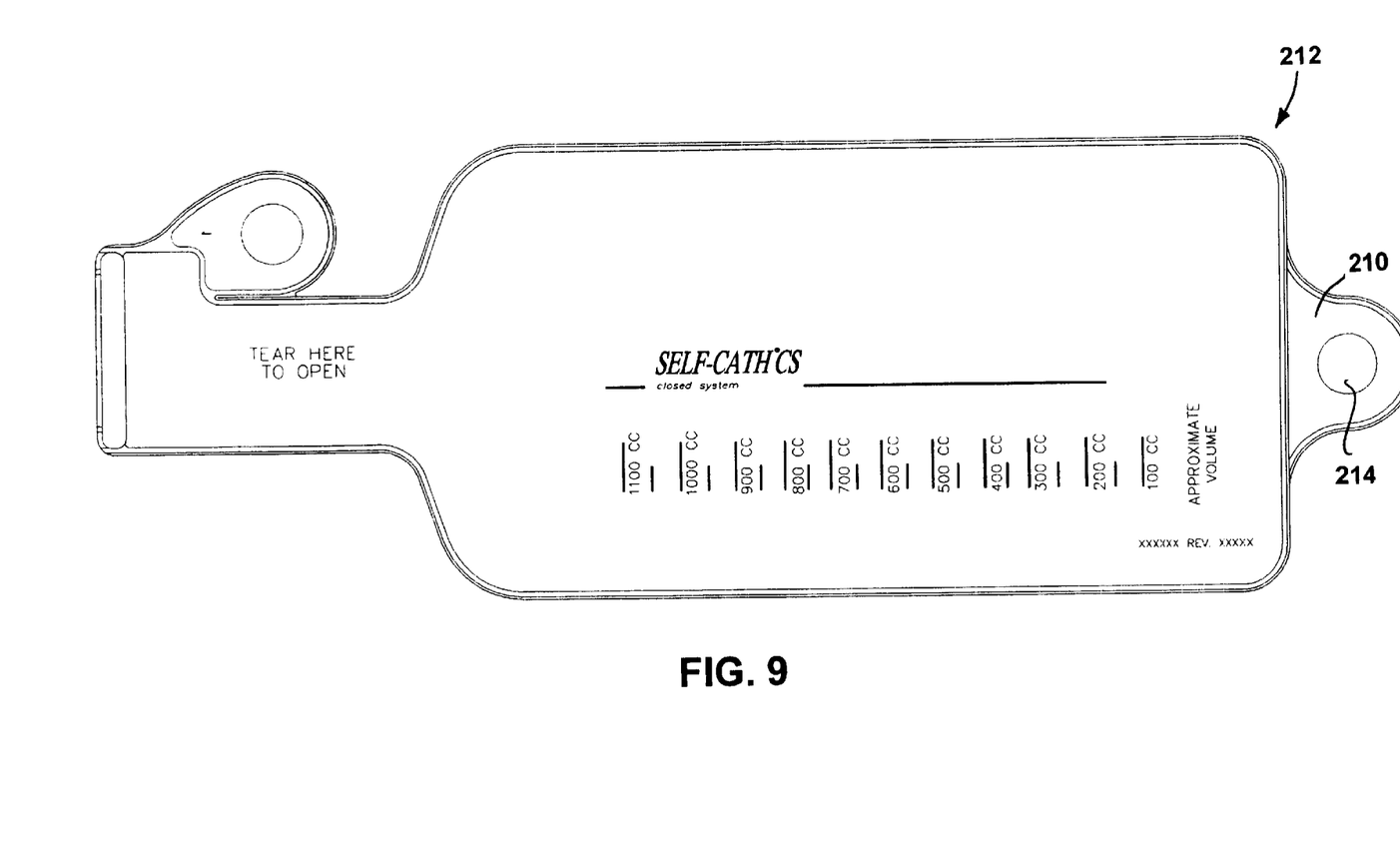
FIG. 9 is a front planar view of a urine collection bag according to a further embodiment of the invention.

The urine collection bag may also include features designed to make the bag easier to hold during emptying, particularly when the user needs to hold the bag with only one hand. For example, as shown in FIG. 9, the bag may include a tab 210 at its distal end 212, with an opening 214 through which the user can insert one or more fingers to hold the bag during draining.

What is claimed is:

1. A urine collection bag for use in a urinary catheter system, comprising:

opposed portions of plastic sheet material that are sealed together around a peripheral edge to define a substantially closed receptacle;

each portion including a surface texture having a depth sufficient to increase the flexibility of the plastic sheet material relative to an otherwise identical plastic sheet material without the surface texture, the surface texture being disposed on an interior surface of the receptacle; and an interface tube having a beveled opening constructed to allow a user to apply pressure with an index finger or thumb from an exterior surface of the receptacle and thereby press the surface texture against a urinary catheter disposed within the receptacle to hold the catheter in place while manipulating the sheet material to advance the catheter out of the receptacle.

2. The urine collection bag of claim 1 wherein the plastic sheet material is a noiseless material.

3. The urine collection bag of claim 2 wherein the noiseless material comprises PVC.

4. A urine collection bag for use in a urinary catheter system, comprising:

opposed portions of plastic sheet material that are sealed together around a peripheral edge to define a substantially closed bag; and a surface texture disposed the opposed surfaces of each of the portions, wherein the surface texture is constructed to increase the friction between the opposed surfaces of the portions and a catheter during gripping of the catheter by a user, relative to the friction exerted by opposed portions of an otherwise identical plastic sheet material without the surface texture.

5. The urine collection bag of claim 4 wherein the surface texture is constructed to provide pockets for receiving lubricant.

6. A closed catheter system comprising:

a urine collection bag including opposed portions of plastic sheet material that are sealed together around a peripheral edge to define a substantially closed bag;

a surface texture disposed on the opposed surfaces of each of the portions; and a catheter disposed within the bag;

wherein the urine collection bag is constructed to allow the catheter to be advanced from the bag by a user, wherein the surface texture is constructed to increase the friction between the opposed surfaces of the portions and the catheter during gripping of the catheter by the user, relative to the friction exert by opposed portions of an otherwise identical plastic sheet material without the surface texture.

7. The closed catheter system of claim 6 wherein the catheter is lubricated.

8. The closed catheter system of claim 7 wherein the surface texture is constructed to provide pockets for receiving lubricant.

9. A urine collection bag for use in a urinary catheter system, comprising:

a reservoir region for containing urine;

extending from the reservoir region, an elongated neck region having an end through which a catheter can be introduced into a user's urethra;

extending from a side portion of the neck region, a tear tab constructed so that pulling the tear tab outwardly from the neck region exposes a pour opening on the side of the neck region, through which urine can be drained from the urine collection bag; and a tab at a distal end of the bag, having an opening through which a user draining the bag can insert one or more fingers.

* * * * *

UNITED STATES PATENT AND TRADEMARK OFFICE
CERTIFICATE OF CORRECTION

PATENT NO. : 6,887,230 B2
DATED : May 3, 2005
INVENTOR(S) : Thomas P. Kubalak et al.

It is certified that error appears in the above-identified patent and that said Letters Patent is hereby corrected as shown below:

Title page,
Item [*] Notice, should read:
-- Subject to any disclaimer, the term of this
patent is extended or adjusted under 35
U.S.C. 154(b) by 236 days --.

Signed and Sealed this

Twenty-second Day of November, 2005

JON W. DUDAS
*Director of the United States Patent and Trademark Office*

UNITED STATES PATENT AND TRADEMARK OFFICE
CERTIFICATE OF CORRECTION

PATENT NO. : 6,887,230 B2 Page 1 of 1
APPLICATION NO. : 10/015485
DATED : May 3, 2005
INVENTOR(S) : Thomas P. Kubalak et al.

It is certified that error appears in the above-identified patent and that said Letters Patent is hereby corrected as shown below:

Title page,
Item [75], Inventors, delete "Plymouth" and insert -- Deephaven --.
Item [56], References Cited, U.S. PATENT DOCUMENTS, insert:
-- 4,988,343  1/1991    Ballan
  5,087,251  2/1992    Heyman et al.
  5,263,946  11/1993   Klug --;
OTHER PUBLICATIONS, "Diokno et al." reference, delete the three occurrences of "+" and insert -- = --.

Column 9,
Line 35, after "disposed" insert -- on --.

Signed and Sealed this

Twenty-seventh Day of June, 2006

JON W. DUDAS
*Director of the United States Patent and Trademark Office*